United States Patent [19]

Lee

[11] Patent Number: 4,956,170

[45] Date of Patent: Sep. 11, 1990

[54] SKIN MOISTURIZING/CONDITIONING ANTIMICROBIAL ALCOHOLIC GELS

[75] Inventor: Andrew S. Lee, Racine, Wis.

[73] Assignee: S. C. Johnson & Son, Inc., Racine, Wis.

[21] Appl. No.: 372,723

[22] Filed: Jun. 28, 1989

[51] Int. Cl.$^5$ .............................................. A61K 7/06
[52] U.S. Cl. ...................................... 424/81; 514/873; 514/944; 252/315.4
[58] Field of Search .................. 424/81; 514/873, 944; 523/105; 252/315.4

[56] References Cited

U.S. PATENT DOCUMENTS

| | | | |
|---|---|---|---|
| 2,054,989 | 9/1936 | Moore | 167/58 |
| 3,215,603 | 11/1965 | Gross et al. | 424/71 |
| 3,427,382 | 2/1969 | Haefele | 424/71 |
| 3,485,915 | 12/1969 | Gerstein et al. | 424/81 |
| 3,609,102 | 9/1971 | Schlossman | 252/522 |
| 3,652,497 | 3/1972 | Junas | 260/47 UA |
| 4,112,121 | 9/1978 | Tenta | 424/346 |
| 4,199,564 | 4/1980 | Silver et al. | 424/80 |
| 4,246,285 | 1/1981 | Van Duzee | 424/358 |
| 4,254,104 | 3/1981 | Suzuki | 424/170 |
| 4,316,887 | 2/1982 | Kamishita et al. | 424/81 |
| 4,389,418 | 6/1983 | Burton | 424/365 |
| 4,464,293 | 8/1984 | Dobrin | 252/547 |
| 4,478,853 | 10/1984 | Chaussee | 424/358 |
| 4,548,807 | 10/1985 | Westfall et al. | 424/45 |
| 4,695,453 | 9/1987 | Tuominen et al. | 424/81 |
| 4,760,096 | 7/1988 | Sakai et al. | 514/944 |

FOREIGN PATENT DOCUMENTS 3543918 6/1987 Fed. Rep. of Germany .

OTHER PUBLICATIONS

Service Bulletin GC-36 Revised, "Carbopol ® Water-Soluble Resins", B. F. Goodrich, Cleveland, Ohio, pp. 15-16, 22-24, 27-28.
Ultracol TM, A 70% Ethyl Alcohol Gel with Emollients, Dexide, Inc., Ft. Worth, Tex., Package Label, 2 pages.
Advertisement, "Alpha 9 Instant Hand Sanitizer", JDS Mfg. Co., Hollywood, Calif., from *Modern Salon*, Aug. 1989, 1 page.

*Primary Examiner*—Merrell C. Cashion, Jr.
*Assistant Examiner*—E. J. Webman

[57] ABSTRACT

This invention relates to a high alcohol content antimicrobial gel composition for frequent use in disinfecting the hands which possesses moisturizing and conditioning agents to counter the drying effects of the alcohol on the skin in manner similar to that provides by hand and body lotions. The gel compositions comprises from about 60-75% ethanol; about 0.4-2% of a thickening agent which is an addition polymer of acrylic acid crosslinked with an unsaturated polyfunctional agent; sufficient neutralizing agent such as diisopropanol amine to neutralize 15-100%, preferably 15-50%, of the carboxyl groups in the thickener; about 0.5-2.5% of a hydrocarbon emollient such as petrolatum; about 0.5-2% of a fatty ester emollient such as isopropyl palmitate; about 0.05-1% of a compatible surfactant such as ceteth-20; 0.5-3% of a fatty alcohol such as cetyl and myristyl alcohol; and about 1-6% of a humectant such as glycerine; and the balance comprising water, there being at least about 20% water present and the gel composition has a viscosity of from about 10,000 centipoise to 100,000 centipoise (10 to 100 pascal second) at 25° C.

12 Claims, No Drawings

SKIN MOISTURIZING/CONDITIONING ANTIMICROBIAL ALCOHOLIC GELS

TECHNICAL FIELD

This invention relates to an antimicrobial alcoholic gel composition for disinfecting the hands which also possesses moisturizing and conditioning agents to counter the drying effects of the alcohol on the skin.

BACKGROUND ART

Compositions containing at least 52% by weight of ethanol or isopropanol are known to be antimicrobial and thus useful in disinfecting surfaces. Compositions of this type which are in the form of ethanolic gels are commercially available for institutional use such as in hospitals and clinics under the trademarks DELIVER(TM) Alchohol Gel from S. C. Johnson & Son, Inc. of Racine, Wisconsin and ULTRACOL(TM) 70% Ethyl Alcohol Gel Hand Rub With Emollients from Dexide, Inc. of Ft. Worth, Texas, Because these products are used frequently during the day in institutions, the drying effect of the alcohol takes a toll on the skin of users of such products. While the Dexide product states that it contains emollients and the Johnson product contains humectants such as glycerine and polyalkylene glycol copolymers along with dimethicone fluids, they do not provide the moisturizing and conditioning properties found in hand and body lotions such as those described in U.S. Pat. No. 4,389,418 to Burton. U.S. Pat. No. 4,478,853 to Chaussee teaches skin conditioning compositions for protecting the skin against dryness which can be in the form of hand and body lotions as well as in the form of a hydroalcoholic gel composition containing from 35–50% and up to 55% of an alcohol such as ethanol or isopropanol along with skin conditioning ingredients which are emollients and humectants and a neutralized, crosslinked polymer of acrylic acid as a thickening agent for use as an afterbath and shower gel product, e.g., as a splash-on skin refresher.

One object of the present invention is to provide a high alcohol content gel composition for frequent use which is antimicrobial owing to the presence of the alcohol while at the same time provides a level of skin conditioning and moisturization to the skin which is more akin to a hand and body lotion.

To accomplish this, a higher level of specific emollients and humectants which include fatty alcohols are employed. U.S. Pat. No. 4,464,293 to Dobrin teaches a liquid cleaner-disinfectant composition for use in wiping down dental operatories. Dobrin teaches the use of 50–91% by volume of ethyl or isopropyl alcohol in the composition as a disinfectant. Dobrin teaches that skin emollients such as AMMONYX(R) LO (lauramine oxide) from Onyx Chemical Corp., "lanolyn", glycerine and cetyl alcohol can be used in these composition in amounts of between 0.5% and 1.5% by volume to prevent drying of the skin by the composition. Another example of a disinfecting composition with emollients like glycerine or sorbitol is the cow teat dip solution taught in U.S. Pat. No. 4,199,564 to Silver et al.

Increased use of such ingredients in a high alcohol gel composition often results in composition instability due to the amount of alcohol present because it is believed that the more hydrophobic ingredients such as petrolatum tend to cause the gel to lose viscosity with time upon storage and to develop into a thin and runny composition. Therefore, another object of this invention is to provide a stable alcoholic gel composition having the above characteristics.

Service Bulletin GC-36 Revised entitled "CARBOPOL(R) Water-Soluble Resins", from B. F. Goodrich Chemical Division of Cleveland, Ohio teaches water-alcohol gels using CARBOPOL 934, 940 AND 941 on pages 15 and 16 and after-shave, hair grooming, sun screening and insect repellent gels on pages 27–28. Pages 22–24 teach hand creams and lotions containing CARBOPOL Resins although these formulations do not contain high amounts of alcohol. U.S. Pat. No. 3,485,915 to Gerstein et al. teaches combinations of CARBOPOL-type resins with hydroxypropyl cellulose as thickening agents for cosmetic compositions, some of which contain ethyl alcohol, e.g., the hair grooming gel of Example 4 contains 63.5 parts by weight of ethyl alcohol. Other than for hair grooming, very high alcohol content gel compositions, i.e., greater than about 60% by weight, are not taught in these references. Another example of a gel hairdressing composition containing up to 60% alchohol is found in U.S. Pat. No. 3,427,382 to Haefele.

U.S. Pat. No. 4,316,887 to Kamishita et al. teaches topically applied compositions containing menthol or camphor which have 20–60% alcohol, water and a neutralized polyacrylic acid thickener to give a viscosity of 2,000 centipoise to 20,000 centipoise (2 to 20 pascal second) after the initial viscosity has been reduced using sodium chloride solution. The sodium chloride solution is used to counteract the viscosity lowering effect of perspiration on the topical composition when it is applied to human skin. No mention of emollients or humectants is made.

A high alcohol content—greater than about 75% by weight—composition for use as a semi-solid rubbing alcohol composition which further contains waxes, paraffin or mineral oil and lanolin or coconut oil is taught in U.S. Pat. No. 2,054,989 to Moore. The waxes are employed to enable the semi-solid composition to be spread evenly on the body. The lanolin and coconut oil are employed to keep the skin soft and pliable as well as to lower the melting point of the composition. Water may or may not be present in these compositions.

SUMMARY DISCLOSURE OF INVENTION

The above and other objects and advantages are provided by a high alcohol content gel composition with skin moisturizing and conditioning properties comprising (a) from about 60 to 75, preferably 60 to 65, weight percent of ethanol, isopropanol and mixtures thereof, preferably (a) is ethanol; (b) from about 0.4 to 2, preferably 0.45 to 0.65, weight percent of a thickening agent which is an addition polymer of acrylic acid crosslinked with an unsaturated polyfunctional agent; (c) a sufficient amount of a compatible neutralizing agent for thickening agent (b) to neutralize from about 15% to 100%, preferably from 15% to 50%, and most preferably, from 15% to 35%, of the acrylic acid carboxyl units present in thickening agent (b), said neutralizing agent being selected from the group consisting of amines of the formula $HO(C_mH_{2m})_2NH$ where m has a value of from 2 to 3, aminomethyl propanol, aminomethyl propanediol, and $H(OCH_2CH_2)_xRN-(CH_2CH_2O)_yH$ where R is a hydrocarbon radical having from 10 to 18 carbon atoms and the sum of x+y has an average value of from about 5 to 25, preferably (c) is $(CH_3CH(OH)CH_2)_2NH$; (d) from about 0.5 to 2.5, preferably 0.75 to 2, weight percent of at least one hydrocarbon emollient selected from the group consisting of petrolatum and mineral oil, preferably petrolatum; (e) from about 0.5 to 2, preferably 0.5 to 1.5, weight percent of at least one fatty ester emollient, preferably isopropyl palmitate; (f) from about 0.05 to 1, preferably 0.1 to 0.5, weight percent of at least one compatible surfactant to stabilize the composition such as a nonionic surfactant, for example a polyethoxylated fatty acid such as ceteth-20; (g) from about 0.5 to 3, preferably 1 to 2.5, weight percent of at least one fatty alcohol having from 12 to 22 carbons atoms; (h) from about 1 to 6, preferably 2 to 4, weight percent of a humectant selected from the group consisting of water soluble polyhydric alcohols having from 2 to 3 hydroxyl groups; and (i) the balance comprising water, there being at least about 20 weight percent water present and the gel composition has a viscosity of from about 10,000 centipoise to 100,000 centipoise (10 to 100 pascal second) at 25° C.

Optionally, the compositions of the present invention can contain small amounts of additional thickeners such as guar gums (0.1 to 0.5 weight percent), silicone fluids such as dimethicone and cyclomethicone (0.05 to 1 weight percent), dyes and fragrances. The surfactant can also be or include an anionic or amphoteric surfactant. These compositions are useful as antimicrobial gels for frequent use in disinfecting the hands in hospitals, clinics and the like as well as for use by ordinary consumers concerned with eliminating bacterial and viral contamination such as that caused by contact with sick individuals in the home.

Best Mode for Carrying Out the Invention

For purposes of this invention, "weight percent" in reference to the gel compositions means weight percent of the total composition unless otherwise indicated.

The compositions of the present invention rely on the presence of from about 60 to 75 weight percent of an alcohol such as ethanol, isopropanol and mixtures thereof to serve as an antibacterial agent. The alcohol can be an anhydrous product or can contain some water such as 190 proof ethanol (95% alcohol). It can be either denatured or pure alcohol. A presently preferred alcohol is ethanol and more preferably, SD Alcohol 40A which is anhydrous ethanol denatured with t-butyl alcohol and sucrose octaacetate.

To obtain a gelled composition, a thickening agent which is an addition polymer of acrylic acid crosslinked with an unsaturated polyfunctional agent such as a polyallyl ether of sucrose is employed. Such polymers are described in U.S. Pat. Nos. 2,798,053 and 3,133,865, have the CTFA (Cosmetic, Toiletry and Fragrance Association) adopted name of "Carbomer" and are commercially available under the tradenames CARBOPOL(R) 934, 940 and 941 from B. F. Goodrich Chemicals Group of Cleveland, Ohio and under the tradenames ACRITAMER 934, 940 and 941 from R.I.T.A. Corporation of Crystal Lake, Illinois. These polymers are used in an amount which is sufficient to obtain a gelled composition of viscosity in the range of 10,000 to 100,000 centipoise (10 to 100 pascal second) at 25° C., and for pump dispenser use, preferably from about 10,000 to 50,000 centipoise (10 to 50 pascal second), and most preferably, from about 10,000 to 20,000 centipoise (10 to 20 pascal second), but not so much as to leave a sticky residue on the skin after the alcohol and water in the composition have evaporated. Typically from 0.4 to 2 weight percent of the total composition and preferably, from about 0.45 to 0.65 weight percent of such a thickener is used. Presently, ACRITAMER 940 is preferred.

Optionally, up to about 0.5 weight percent of other thickeners can be used to improve the gel obtained as well as the skin feel of the composition. For example, from about 0.1 to about 0.5, preferably 0.25, weight percent of a hydroxypropyl guar gum (propylene glycol ether of guar gum) of higher molecular weight and higher degree of substitution such as JAGUAR HP-79 and HP-120 from Alcolac, Inc. of Baltimore, Maryland can be used. It was found that less highly substituted hydroxypropyl guar gums such as JAGUAR HP-8 as well as quaternized hydroxypropyl guar gums such as JAGUAR C14 and HiCare 1000, also from Alcolac, did not give adequate thickening at a 60% ethanol level. The thickeners employed must be capable of thickening the high alcohol content gel compositions of this invention and be capable of leaving a residue on the skin which is not overly sticky and has acceptable tactile characteristics.

It was found that the high alcohol content of these compositions affects the gelling ability of the acrylic polymer thickeners and the composition stability. A stability of at least about two years at room temperature is desirable for commercial products. As is known, the best thickening results are obtained when the acrylic polymer thickening agent is neutralized to render it water soluble. From about 15% to 100% of the carboxyl groups present in the acrylic acid polymer are neutralized with a compatible neutralizing agent. By the term "compatible", it is meant that the neutralizing agent is capable of causing the thickener thicken and gel the composition to the desired viscosity.

It was found that with the compositions of the present invention, triethanolamine, sodium hydroxide, monoethanolamine, and dimethyl stearylamine were not compatible as neutralizing agents because they did not adequately form a gel of deirable viscosity when used to neutralize 25%–35% of the carboxyl groups in ACRITAMER 940 thickening agent in a 60 weight percent ethanol composition. Increasing the degree of neutralization with triethanolamine resulted in a low viscosity liquid composition. However, neutralizing agents such as $HO(C_mH_{2m})_2NH$ where m has a value of from 2 to 3, aminomethyl propanol, aminomethyl propanediol, and $H(OCH_2CH_2)_xRN-(CH_2CH_2O)_yH$ where R is a hydrocarbon radical having from 10 to 18 carbon atoms and the sum of x+y has an average value of from about 5 to 25 such as PEG-25 cocamine (i.e., where R are hydrocarbon groups derived from coconut fatty acid and the sum of x+y is about 25) can be employed, presently, diisopropanolamine—$(CH_3CH(OH)CH_2)_2NH$—is preferred. Other examples of ethoxylated amines are polyoxyethylene (5) cocoamine ("PEG-5 cocamine"); polyoxyethylene (10) cocoamine ("PEG-10 cocamine"); polyoxyethylene (15) cocoamine ("PEG-15 cocamine"); polyoxyethylene (25) cocoamine; polyoxyethylene (5) octadecylamine ("PEG-5 stearamine"); polyoxyethylene (10) octadecylamine ("PEG-10 stearamine"); polyoxyethylene (15) octadecylamine ("PEG-15 stearamine"); polyoxyethylene (20) octadecylamine; polyoxyethylene (25) octadecylamine; polyoxyethylene (5) tallowamine ("PEG-5 tallow amine"); polyoxyethylene (15) tallowamine ("PEG-15 tallow amine"); polyoxyethylene (5) oleylamine ("PEG-5 oleamine"); polyoxyethylene (15) oleylamine ("PEG-15 oleamine"); polyoxyethylene (5) soyaamine ("PEG-5 soyamine"); polyoxyethylene (10) soyaamine ("PEG-10 soyamine"); polyoxyethylene (15) soyaamine ("PEG-15 soyamine"); and polyoxyethylene (25) soyaamine. A number of these long chain amines are available commercially under the tradename of ETHOMEEN from Akzo Chemie America, Armak Chemicals of Chicago, Illinois. Some amines such as PEG-25 cocamine impart a slight amine odors to the composition which may be masked with a fragrance. PEG-25 cocamine was found to be very efficient in building viscosity in the high alcoholic gel compositions as can be seen from the Examples below.

It was found that with diisopropanolamine, increasing the level of neutralization from 25% gave higher viscosity products, but it was found that the viscosity stability decreased with increasing degree of neutralization. Therefore it is preferred that from about 15% to 50%, and most preferably, from 15% to 35% of the carboxyl groups present in the thickener be neutralized. The viscosity of the gel composition tends to be more stable when lower levels of neutralization are employed. A level of 15–35% neutralization is preferred when only the acrylic acid polymer thickening agent is employed while the compositions tend to be the most stable in the range of 15–50% when an additional thickening agent such as hydroxypropyl guar is also present. It was also found that the initial viscosity of the gel varies inversely with the level of alcohol present.

The viscosity of the compositions was found to increase dramatically when the ethanol concentration was decreased below 60% by weight by substituting water for ethanol. Gel stability also suffers when relatively high amounts of alcohol are used. Thus, the viscosity behavior of compositions containing high amounts, i.e., greater than 60 weight percent and particularly at greater than 60%, of alcohol was quite different than for compositions with lower amounts of alcohol.

The composition contains from about 0.5 to 2.5 weight percent of at least one hydrocarbon emollient such as petrolatum and mineral oils of the type known in the art for use in cosmetic compositions. Petrolatum is presently preferred. "Petrolatum" also includes mixtures of hydrocarbon materials which resemble petrolatum in appearance and consistency such as a mixture formed by melting substances such as paraffin wax or microcrystalline wax and the like with mineral oil. More preferably, 0.75 to 2 percent by weight of a hydrocarbon emollient is present.

From about 0.5 to 2 weight percent of at least one fatty acid ester emollient derived from fatty acids or fatty alcohols having from about 12 to 22 carbon atoms are employed. Examples of such esters are methyl, isopropyl and butyl esters of fatty acids such as isopropyl palmitate, isopropyl myristate, isopropyl isostearate, isostearyl isostearate, diisopropyl sebacate, and propylene glycol dipelargonate, as well as 2-ethylhexyl isononoate, 2-ethylhexyl stearate, $C_{12}$–$C_{16}$ fatty alcohol lactates such as cetyl lactate and lauryl lactate, isopropyl lanolate, 2-ethylhexyl salicylate, oleyl myristate, oleyl stearate, oleyl oleate, hexyl laurate, isohexyl laurate and mixtures of the same.

The composition further contains from about 0.05 to 1 weight percent, preferably from 0.1 to 0.5 weight percent, of at least one "compatible" surfactant wherein "compatible" means capable of stabilizing the composition so that the gel does not separate into distinct layers upon storage at room temperature and which does not react with the other ingredients present to result in such a separation. Thus, nonionic surfactants—which typically do not react with other components—are preferred although it may be possible to use anionic or amphoteric surfactants, including zwitterionic surfactants, if they are compatible with the gel composition.

One example of presently preferred nonionic surfactants are polyethoxylated fatty alcohols of the formula $R'O(CH_2CH_2O)_xH$ where $R'$ is a hydrocarbon radical of from about 12 to 22 carbon atoms and $x$ has a value of from about 2 to 100 and more preferably, from about 2 to 25. The RO— group in the formula can be derived from fatty alcohols having from about 12 to 22 carbon atoms such as lauryl, myristyl, cetyl, hexadecyl, stearyl, isostearyl, hydroxystearyl, oleyl, ricinoleyl, behenyl, and erucyl alcohols, and 2-octadecanol. An example of such surfactants is ceteth-20 (cetyl ether of polyethylene oxide having an average of about 20 ethylene oxide units). This and other such nonionic surfactants are commercially available under the tradename "BRIJ" from ICI Americas, Inc. of Wilmington, Delaware.

Other examples of nonionic surfactants are those typically used in cosmetics such as alkyl phenols with 6 to 12 carbon in the alkyl chain condensed with 2 to 25 moles of ethylene oxide; mono— and di-fatty acid esters of ethylene glycol wherein the fatty acid moiety contains from about 12 to 22 carbon atoms; fatty acid monoglycerides wherein the fatty acid moiety contains from about 12 to 22 carbon atoms; fatty acid esters of sorbitol, sorbitan, polyoxyethlene sorbitol, and polyoxyethylene sorbitan where the fatty acid moiety contains from about 12 to 22 carbon atoms. Such surfactants are well known and many are commercially available.

The compositions also contain from about 0.5 to 3 weight percent of at least one fatty alcohol having from 12 to 22 carbon atoms. The same alcohols specified for use in the above polyethoxylated alcohols can be employed by themselves as this component of the gels. A 2:1 to 5:1 by weight blend of cetyl alcohol to myristyl alcohol has been found to be useful with the 5:1 blend being presently preferred. Stearyl alcohol has also been found to be useful. More preferably, the total fatty alcohol content in the compositions is from about 1 to 2.5 weight percent.

Humectants are present in an amount of from about 1 to 6 weight percent and are selected from the group consisting of water soluble polyhydric alcohols having from 2 to 3 hydroxyl groups such as 1,2-propylene glycol, dipropylene glycol, polyethylene glycol of molecular weight up to about 6,000, 1,3-butylene glycol, 1,2,6-hexanetriol, glycerine and mixtures thereof. Glycerine is presently preferred. Preferably, the humectant is present as from about 2 to 4 weight percent of the total composition.

Water comprises the balance of the composition. Deionized water is preferred. There should be a sufficient amount of water to provide a thickened gel composition. Generally, at least about 20 weight percent of the composition should be water, more preferably at least 25% and most preferably, at least 28%.

To improve lubricity, a silicone fluid such as a dimethylpolysiloxane or other conventional organopolysiloxanes can be used in amounts of from about 0.05 to 1 weight percent. In general, the viscosity of the silicone fluid at a temperature of 25° C. is from about 5 centistokes to about 12,500 centistokes ($5 \times 10^{-6}$ to $1.25 \times 10^{-2}$ square meters per second—"$m^2/sec$"). Typical organopolysiloxanes which can be used are dimethylpolysiloxane (CTFA name-dimethicone which is a dimethylpolysiloxane end-blocked with trimethylsiloxy units), diethylpolysiloxane, dimethyl-diphenyl-polysiloxane, and the like. Volatile linear and cyclic polydimethylsiloxanes such as hexamethyldisiloxane, polydimethylcyclosiloxane (CTFA-cyclomethicone), and trimethylsilyl end-blocked polydimethylsiloxane having a viscosity in the range of from about 0.65 centistokes to about 5 centistokes ($6.5 \times 10^{-7}$ to $5 \times 10^{-6}$ $m^2/sec$) can also be included as part of the silicone fluid content.

Other conventional additives to cosmetic compositions such as fragrances, dyes, corrosion inhibitors, etc. can also be included provided that they are compatible with the gel composition.

The presently preferred method for making the gel compositions of the present invention is as follows: The addition polymer of acrylic acid thickener is dispersed in the alcohol in a first vessel at room temperature—about 77° F. (25° C.). After a relatively homogeneous dispersion is formed in the first vessel, the fatty ester emollient is then incorporated into the dispersion. In a second separate vessel, any optional water soluble thickener employed such as guar gum is dispersed in the water and heated to facilitate solution of the thickening agent, typically to about 135°–170° F. (57.2°–76.7° C.) with 135°–150° F. (57.2°–65.6° C.) being more preferred. If no such optional thickener is employed, the water is simply heated. Then any silicone fluid is added to the heated water with vigorous agitation followed by the addition of humectant, hydrocarbon emollient, fatty alcohol and, the surfactant. Agitation is continued until a uniform emulsion is formed and then the emulsion is cooled to about 80°–85° F. (26.7°–29.4° C.) and adjusted for any water loss that might have occurred. The contents of the first vessel containing the alcohol are added to the second vessel with agitation. The contents of the second vessel may be added to the first although the former procedure is preferred because the alcoholic contents of the first vessel are typically very fluid and readily poured or pumped into the second vessel. When a homogeneous solution is obtained, any fragrances and dyes are added. The neutralizing agent is then added whereupon the contents of the vessel thickens to a gel. The composition can then be adjusted for any alcohol loss that might have occurred and the gel can then be packaged in containers for use.

Industrial Applicability

Compositions made in accordance with the above method are useful in institutions such as hospitals, nursing homes and clinics where frequent contact with sources of bacteria and viruses are possible and, thus, a frequent need for disinfecting the hands arises. The user simply spreads the gel over clean hands as one would normally use a hand lotion, rubbing the gel over the hands until they are dry. The contact with the alchohol disinfects the hands and the emollients and humectants leave behind a sufficient amount of residue to reduce the drying effects of the alcohol on the skin. Likewise, such gel compositions can be used in the home for hygienic purposes such as after contacting a sick individual.

The following Examples are provided to show various aspects of the invention without departing from the scope and spirit of the invention. Unless otherwise indicated, such as in reference to percentages of carboxyl radicals being neutralized which are on a stoichiometric basis, all parts and percentages used in the Examples are by weight. In the Examples, the viscosities reported were obtained at 25° C. using a Brookfield Viscosimeter Model No. LVT using a #4 spindle at 30 r.p.m. after 30 seconds. Examples 2, 4 and 20 used 12 r.p.m. instead of 30 r.p.m. and Example 12 used 6 r.p.m. due to their higher viscosity. In the Examples, "% Neutralization" is the percent of carboxyl groups neutralized in the acrylic polymer thickener by the amine.

The ingredients used in the compositions were:

ACRITAMER 940—A polymer of acrylic acid crosslinked with an unsaturated polyfunctional agent, from R.I.T.A. Corporation, equivalent weight reported to be 75.5.

BRIJ 58—Ceteth-20 from ICI Americas, Inc.

DOW CORNING(R) 225 Fluid—Dimethicone of 9.5 centistoke ($9.5 \times 10^{-6}$ $m^2/sec$) viscosity at 25° C. from Dow Corning Corporation of Midland, Michigan.

ETHOMEEN C/25—Polyoxyethylene (25) cocamine from Akzo Chemie America.

JAGUAR HP-120—A highly substituted hydroxypropyl guar gum from Alcolac.

SD Alcohol 40A—Anhydrous denatured ethanol.

EXAMPLES 1–4

These Examples illustrate the production of compositions of the present invention which are useful as antimicrobial gel compositions for the hands. The formulas for each composition in parts by weight were as follows:

| Ingredient | Example 1 | Example 2 |
|---|---|---|
| SD Alcohol 40A | 62.00 | 62.00 |
| ACRITAMER 940 | 0.50 | 0.50 |
| JAGUAR HP-120 | 0.25 | 0.25 |
| Cetyl Alcohol | 1.67 | — |
| Myristyl Alcohol | 0.33 | — |
| Stearyl Alcohol | — | 1.25 |
| Isopropyl Palmitate | 1.00 | 0.75 |
| DOW CORNING 225 Fluid | 0.08 | 0.06 |
| Glycerine | 4.00 | 3.00 |
| Petrolatum | 1.33 | 1.00 |
| BRIJ 58 | 0.17 | 0.12 |
| Diisopropanolamine (85%) | 0.36 | 0.52 |
| Fragrance | 0.10 | 0.10 |
| Deionized Water | 28.21 | 30.45 |
| Total | 100.00 | 100.00 |
| pH | 7.45 | 7.71 |
| Viscosity | | |
| Centipoise | 14,320 | 46,850 |
| Pascal second | 14.32 | 46.85 |
| % Neutralization | 35 | 50 |

Examples 1 and 2 were prepared by dispersing the ACRITAMER 940 slowly into the alcohol with good agitation at room temperature in one vessel. After the ACRITAMER 940 was dispersed, the isopropyl palmitate was dissolved into the mixture.

In a second vessel, the JAGUAR HP-120 was dispersed into the water which was then heated to 135° F. (57.2° C.). The following was then added in order with good agitation: DOW CORNING 225 Fluid, glycerine, petrolatum, and cetyl alcohol and myristyl alcohol (Example 1) or stearyl alcohol (Example 2). In Example 2, the contents were heated to 150° F. (65.6° C.) before the stearyl alcohol was added to facilitate melting and dispersion of that fatty alcohol. After all of the ingredients were liquified, the BRIJ 58 was added. The mixture was agitated for an additional 10 minutes at the previously noted temperatures and then cooled to 75°–80° F. (23.9°–26.7° C.). Any water lost in the process was added back to the vessel.

The contents of the first vessel were added to the second vessel with good agitation. The fragrance was then added and mixing was continued until the mixture was homogeneous. The diisopropanolamine was added and agitation was continued until the gelled composition was homogeneous. Any alcohol lost in the processing was then added back to each composition with agitation to obtain the gel composition.

Example 3 had the same formulation as Example 1, but used 0.05 parts of fragrance and had 0.05 parts more of water. It was made by a slightly different process involving dispersing only the ACRITAMER 940 into the ethanol in a first vessel. The JAGUAR HP-120 was then dispersed into the water in a second vessel with good agitation followed by heating the contents of the second vessel to 150° F. (65.6° C.). At temperature, the following ingredients were then added in order with good agitation: isopropyl palmitate, DOW CORNING 225 Fluid, petrolatum, glycerine, cetyl alcohol and myristyl alcohol. The contents were agitated until the fatty alcohols were melted and dispersed into the mixture. The BRIJ 58 was added and agitation was continued until it had dispersed. The contents were then agitated for an additional 10 minutes at 150° F. (65.6° C.). The contents of the second vessel were cooled to 80°–85° F. (26.7°–29.4° C.) and adjusted for water loss. The contents of the first vessel were then added to the contents of the second vessel with good agitation followed by the fragrance. The diisopropanolamine was then added and the contents were stirred until a uniform gel was obtained. The contents were adjusted for alcohol loss and agitated until homogeneous to obtain Example 3 which had a pH of 7.56 and viscosity of 14,720 centipoise (14.72 pascal second).

Example 4 had the same formulation as Example 2, but had 0.05 parts of fragrance and 0.05 more parts of water. It was prepared in the same manner as used for Example 3, but the glycerine was added before the petrolatum and the contents of the second vessel were heated to 170° F. (76.7° C.) just before the addition of the stearyl alcohol due to the higher melting point of the stearyl alcohol. Example 4 had a pH of 7.99 and viscosity of 41,850 centipoise (41.85 pascal second).

EXAMPLE 5

In this comparative example, a high alcohol content gel composition was prepared for purposes of comparison with Examples 3 and 4. This composition lacked humectants and fatty alcohol emollients. Example 5 had the following composition:

| Ingredient | Example 5 |
| --- | --- |
| SD Alcohol 40A | 65.000 |
| Dyes (0.1% solution) | 0.380 |
| ACRITAMER 940 | 0.550 |
| BRIJ 721 | 0.100 |
| Isopropyl Palmitate | 1.000 |
| Petrolatum | 1.000 |
| Diisopropanolamine (85%) | 0.281 |
| Fragrance | 0.100 |
| Deionized Water | 31.589 |
| Total | 100.000 |
| pH | 7.10 |
| Viscosity | |
| Centipoise | 13,800 |
| Pascal second | 13.80 |

| Ingredient | Example 5 |
| --- | --- |
| % Neutralization | 100 |

This gel composition was made by combining the water and dyes with good agitation until the mixture was homogeneous. The ACRITAMER 940 was then added slowly with good agitation to the mixture. After the addition was complete, the agitation was continued for an additional 15 minutes. The mixture was then heated to 135° F. (57.2° C.) and then the petrolatum was added. Agitation was continued until the petrolatum had melted. The isopropyl palmitate was then added followed by the BRIJ 58 with mixing after each addition was complete. The mixture was cooled to 80° F.–85° F. (26.7° C.–29.4° C.) and the alcohol was added. The fragrance was then added and the mixture was agitated until it was homogeneous. The diisopropanolamine was then added and mixing was continued until the gelled composition was homogeneous.

EXAMPLE 6

In this Example, the compositions of Examples 3 and 4 were tested against comparative Example 5 and a commercial hand and body lotion—VASELINE brand Intensive Care Lotion (hereinafter "VICL") from Cheesebrough-Pond's Inc. of Greenwich, Connecticut—by a trained skinfeel descriptive panel of 7 panelists over a 5 day period of time.

Prior to starting the testing, the panelists washed their forearms with triethanolamine lauryl sulfate solution in water and drew four 2 inch (5.1 cm) circles on each forearm. Two circles were used to evaluate each product—one for rub-out and one for point of absorption and afterfeel. In each evaluation, 0.2 cc of the gel to be tested or 0.1 cc of VICL was applied to the first circle on panelist's forearm by the test administrator and rubbed 10 times by the panelist. Rub-out properties were evaluated by the panelist. A second amount of the same product was applied to the second circle by the test administrator and rubbed by the panelist until the point of drag was reached. The panelist then set a stopwatch and evaluated skinfeel properties at the point of drag, i.e., when the volatile portion of the composition had essentially evaporated and the lubricity of the composition was lost, and at three and fifteen minutes later. Separately, the gel or lotion was evaluated for appearance and pick-up attributes, i.e., an evaluation of the gel or lotion for consistency, firmness, stringiness and stickiness. Four samples were evaluated per session and each panelist attended four sessions. The samples were presented in a random order and were blind-labeled with a code number so the panelists could not identify which sample they were evaluating. Each panelist filled out a questionnaire which was used to reach the following conclusions.

The conclusions of the panel review were that the gels of Examples 3 and 4 differed from comparative Example 5 by having a more opaque appearance and a more stringy texture. Example 4 was found to feel firmer than Example 5. These characteristics were deemed to suggest improved gel integrity over Example 5 and may provide users with better product control during application.

Examples 3–5 were deemed to be easier to spread, felt more cool and wet, and felt less greasy during rub-out than VICL. Examples 3-5 absorbed faster than VICL. Since these are characteristics of a gel composition, it was doubltful that one would obtain parity with the VICL in rub-out due to the differences in composition between the gels and VICL.

Both Examples 3 and 4 were deemed to show improvements over Example 5 when compared to VICL, particularly at the point of drag and afterfeel at 3 and at 15 minutes after absorbing. Example 3 was judged to feel more slippery on skin than VICL at the 3 minute afterfeel test, and was judged to be equal to VICL on all other afterfeel attributes tested. Relative to VICL, Example 4 was judged to feel less slippery and more sticky at the point of drag, less greasy at 3 minute afterfeel, and was less greasy and less oily than VICL at 15 minute afterfeel.

Relative to Example 4, Example 3 was deemed to feel more slippery at the point of drag, more slippery and oily at 3 minute afterfeel and made the skin look more shiny and feel more sticky and more greasy at 15 minute afterfeel.

Thus, Examples 3 and 4 were both judged to provide a skinfeel more similar to the VICL lotion than Example 5.

EXAMPLES 7-9

The following formulations (in parts by weight) illustrate further examples of the gel compositions of the present invention:

| Ingredient | Ex. 7 | Ex. 8 | Ex. 9 |
|---|---|---|---|
| SD Alcohol 40A | 62.00 | 62.00 | 62.00 |
| ACRITAMER 940 | 0.50 | 0.55 | 0.55 |
| Cetyl Alcohol | — | 2.00 | 1.50 |
| Myristyl Alcohol | — | 1.00 | 0.75 |
| Stearyl Alcohol | 2.50 | — | — |
| Isopropyl Palmitate | 0.60 | 0.75 | 0.75 |
| DOW CORNING 225 Fluid | 0.05 | 0.063 | 0.063 |
| Glycerine | 2.40 | 3.00 | 3.00 |
| Petrolatum | 0.80 | 1.00 | 1.00 |
| BRIJ 58 | 0.25 | 0.25 | 0.20 |
| Diisopropanolamine (85%) | 0.52 | 0.281 | 0.281 |
| Fragrance | — | 0.05 | 0.05 |
| Deionized Water | 30.38 | 29.056 | 29.856 |
| Total | 100.00 | 100.000 | 100.000 |
| pH | 7.26 | 6.98 | 6.83 |
| Viscosity | | | |
| Centipoise | 15,020 | 11,480 | 12,200 |
| Pascal second | 15.02 | 11.48 | 12.20 |
| % Neutralization | 50 | 25 | 25 |

The procedure used to make Example 7 was to disperse the ACRITAMER 940 in the water at room temperature followed by heating the dispersion to 150° F. (65.6° C.). At 150° F. (65.6° C.), the following were added in order with good agitation allowing each to disperse into the mixture before adding the next ingredient: isopropyl palmitate, DOW CORNING 225 Fluid, glycerine, petrolatum, BRIJ 58 and stearyl alcohol. The mixture was heated to 170° F. (76.7° C.) after the addition of the stearyl alcohol to permit it to melt and disperse well. The temperature was held at 170° F. (76.7° C.) for 10 minutes to allow the stearyl alcohol to melt and the mixture was then cooled to 80° F.–85° F. (26.7° C.–29.4° C.) and adjusted for water loss during processing. The ethanol was then added with good agitation followed by the ACRITAMER 940. Agitation was continued until the ACRITAMER 940 was well dispersed and then the diisopropanolamine was added with good agitation. Agitation was continued until the gel composition was homogeneous. The composition was adjusted for ethanol loss and agitation was continued until the composition was homogeneous. The gel composition was opaque in appearance.

The procedure used to make Example 8 was to heat the water to 150° F. (65.6° C.) and then add the following in order with good agitation: isopropyl palmitate, DOW CORNING 225 Fluid, glycerine, petrolatum, cetyl alcohol, myristyl alcohol, and BRIJ 58. The mixture was then cooled to 80° F.–85° F. (26.7° C.–29.4° C.) and adjusted for water loss during processing. The ethanol was then added with good agitation followed by the ACRITAMER 940. Agitation was continued until the ACRITAMER 940 was well dispersed, the fragrance was added, and then the diisopropanolamine was added with good agitation. Agitation was continued until the gel composition was homogeneous. The composition was adjusted for ethanol loss and agitation was continued until the gel composition was homogeneous.

The procedure used to make Example 9 was the same as was used for Example 8.

The gel of Example 7 was opaque. The gels of Examples 8-9 were translucent gels with no crystalline structure evident when observed under a microscope at 100× magnification.

EXAMPLE 10

Examples 7-9 were evaluated versus two commercially available hand and body lotions: CUREL(TM) Moisturizing Lotion (hereinafter "CML") from S. C. Johnson & Son, Inc. of Racine, Wisconsin and the VASELINE brand Intensive Care Lotion ("VICL") used in Example 6. It was believed that neither CML nor VICL contained ethanol or isopropanol in any significant amount.

This testing was conducted by a trained skinfeel descriptive panel of 5 panelists and a test administrator over a 3 week period of time in the same manner as described for the test in Example 6, except the skinfeel after 15 minutes was not evaluated. Each panelist attended six sessions and four samples were evaluated during each session. The test administrator applied 0.1 cc of either CML or VICL or 0.2 cc of one of the gel compositions of Examples 7-9 as described in Example 6. More of the latter composition was used because more of the gel is to be used to properly disinfect the hands. The conclusions from the testing were as follows:

The gels were found to melt faster, feel cooler and wetter during rub-out, and absorb faster than the CML or VICL. All gels tested looked thicker than VICL, but thinner than CML.

As to the VICL versus the gel compositions, the gels tested were judged equal to VICL on most skinfeel properties tested at the point of drag and three minutes thereafter. Some differences were identified between VICL and the individual gels tested. VICL was judged to feel less sticky than Example 7 at the point of drag. VICL made the skin less shiny than Example 8 three minutes after reaching the point of drag. VICL was judged to feel more greasy than Examples 8 and 9 during rub-out.

The gel compositions tested also differed from CML in texture and in critical afterfeel attributes. All gel compositions tested were judged to feel less firm, less sticky and less stringy than CML. The gels were also easier to spread and felt less greasy than CML during rub-out. While the gels absorbed faster, they were judged to feel similar to CML at the point of drag. The skinfeel differences were judged to be more pronounced three minutes after reaching the point of drag where the gels left less product residue on the skin and felt more slippery (more like untreated skin) than CML. These skinfeel similarities and differences between the gels and the CML at the point of drag and 3 minutes thereafter were thought to suggest that the immediate skin moisturization and conditioning provided by the gels will not be as long lasting as the CML. The gels were judged to be significantly different from the CML and thus presumably noticeable to the consumer.

However, it is recognized that the gel products are not hand and body lotions and the intended purpose was to add a significantly increased level of moisturization and conditioning not possessed by prior art gel compositions containing a significant level of alcohol. The gels are intended to be used a number of times daily which will tend to dry the skin by stripping away natural oils. The moisturizing and conditioning ingredients of the gels of the present invention replace some of those natural oils each time the hands are disinfected and thus act similar to a hand and body lotion in that regard.

Additionally, the CML was judged less sticky than Example 7 at the point of drag. CML was judged to provide less skin gloss than Example 8 during afterfeel testing.

Between the gel compositions alone, few differences were identified. Example 7 was judged to be less cool during rub-out than the other gel compositions tested and provided less gloss during afterfeel than Example 8. Example 9 was judged to be less greasy than Example 7 during rub-out. With the exception of coolness during rub-out for Example 7, differences identified in the gel compositions were deemed to be small and not expected to be perceived by typical consumers.

EXAMPLES 11-17

In these Examples, various neutralizing agents were employed to neutralize 35% of the carboxyl units present in the ACRITAMER 940 thickening agent used in the formulation. The formula and procedure used was the same as was used in Example 1, but the base amount of water was 25.82 parts instead of the 28.21 parts of water and the 0.36 parts of diisopropanolamine used in Example 1. A combination of additional water and the neutralizing agent being tested was used in addition to the base amount of water to obtain a total formula with 100 parts.

In comparative Example 11, 0.41 parts of triethanolamine (85% solution) was used along with 2.34 parts of additional water. The resulting gel composition had a pH of 7.75 and a viscosity of 5,900 centipoise (5.9 pascal second) which is outside of the desired viscosity range.

In Example 12, 2.00 parts of ETHOMEEN C/25 was used along with 0.75 parts of additional water. The resulting gel composition had a pH of 8.27 and a viscosity of 88,000 centipoise (88 pascal second) which is within the desired viscosity range.

In comparative Example 13, 0.41 parts of monoethanolamine (25% solution) was used along with 2.34 parts of additional water. The resulting composition had a pH of 7.51 and had a viscosity similar to water, no gel formed.

In comparative Example 14, 0.93 parts of sodium hydroxide (10% solution) was used along with 1.82 parts of additional water. The resulting composition had a pH of 7.07 and had a viscosity similar to water, no gel formed.

In comparative Example 15, 2.75 parts of stearyl dimethylamine was used along with no additional water. The resulting composition had a pH of 7.17 and had a viscosity similar to water, no gel formed.

In Example 16, 0.21 parts of aminomethyl propanol, i.e., 2-amino-2-methyl-1-propanol, was used along with 2.54 parts of additional water. The resulting gel composition had a pH of 7.32 and a viscosity of 14,960 centipoise (14.96 pascal second) which is within the desired viscosity range.

In Example 17, 0.36 parts of diisopropanolamine (85%) was used along with 2.39 parts of additional water to repeat Example 1. The resulting gel composition had a pH of 7.55 and a viscosity of 14,400 centipoise (14.4 pascal second) which is within the desired viscosity range.

EXAMPLES 18-20

In Example 18, anhydrous isopropanol was substituted for the ethanol used in Example 1. The resulting gel composition had a pH of 7.25 and a viscosity of 4,180 centipoise (4.18 pascal second). An additional amount of diisopropanolamine was added to this composition to neutralize a total of 50% of the carboxyl groups present in the ACRITAMER 940. The resulting gel had a pH of 7.36 and a viscosity of 5,260 centipoise (5.26 pascal second) which is outside the desired viscosity range. A further additional amount of diisopropanolamine was added to this composition to neutralize a total of 100% of the carboxyl groups present in the ACRITAMER 940. The resulting gel had a pH of 8.45 and a viscosity of 14,440 centipoise (14.44 pascal second) which is within the desired viscosity range. Thus, diisopropanolamine was not as efficient at building viscosity for an isopropanol-containing gel composition as it was for one containing ethanol.

In Example 19, the composition of Example 18 was repeated, but instead of diisopropanolamine, 1 part of ETHOMEEN C/25 and 27.57 parts of water were used to neutralize 17.5% of the acrylic carboxylic acid groups in the ACRITAMER 940. The resulting gel had a pH of 7.25 and a viscosity of 14,020 centipoise (14.02 pascal second) which is well within the desired viscosity range despite the low degree of neutralization and the use of isopropanol as the alcohol.

Example 20 was a repeat of Example 19, but using 26.57 parts of water and 2 parts of ETHOMEEN C/25 to neutralize 35% of the acrylic carboxylic acid groups. The resulting gel had a pH of 7.87 and a viscosity of 42,600 centipoise (42.60 pascal second) which is within the desired viscosity range.

EXAMPLE 21

This Example illustrates the use of higher levels of emollients and humectant. Using the procedure of Example 9, the following formulation—in parts by weight—was prepared: SD Alcohol 40A—62.00; myristyl alcohol—0.75; cetyl alcohol—1.50; ACRITAMER 940—0.50; BRIJ 58—0.20; isopropyl palmitate—1.50; glycerine—6.00; petrolatum—2.00; DOW CORNING 225 Fluid—0.125; diisopropanolamine (85% solution)—0.52; and deionized water—24.905. The ACRITAMER 940 was 50% neutralized with diisopropanolamine. The resulting gel composition was translucent; showed the presence of oil droplets under 100× magnification, but showed no crystalline structure; had a pH of 7.56 and a viscosity of 10,760 centipoise (10.76 pascal second).

What I claim is:

1. A high alcohol content gel composition with skin moisturizing and conditioning properties comprising
   (a) from about 60 to 75 weight percent of ethanol, isopropanol or mixtures thereof;
   (b) from about 0.4 to 2 weight percent of a thickening agent which is an addition polymer of acrylic acid crosslinked with an unsaturated polyfunctional agent;
   (c) a sufficient amount of a compatible neutralizing agent for thickening agent (b) to neutralize from about 15% to 100% of acrylic acid carboxyl units present in thickening agent (b), said neutralizing agent being selected from the group consisting of amines of the formula $HO(C_mH_{2m})_2NH$ where m has a value of from 2 to 3, aminomethyl propanol, aminomethyl propanediol, and $H(OCH_2CH_2)_xRN(CH_2CH_2O)_yH$ where R is a hydrocarbon radical having from 10 to 18 carbon atoms and the sum of x+y has an average value of from about 5 to 25;
   (d) from about 0.5 to 2.5 weight percent of at least one hydrocarbon emollient selected from the group consisting of petrolatum and mineral oil;
   (e) from about 0.5 to 2 weight percent of at least one fatty ester emollient;
   (f) from about 0.05 to 1 weight percent of at least one compatible surfactant to stabilize the composition;
   (g) from about 0.5 to 3 weight percent of at least one fatty alcohol having from 12 to 22 carbons atoms;
   (h) from about 1 to 6 weight percent of a humectant selected from the group consisting of water soluble polyhydric alcohols having from 2 to 3 hydroxyl groups; and
   (i) the balance comprising water, there being at least about 20 weight percent water present and the gel composition has a viscosity of from about 10,000 centipoise to 100,000 centipoise at 25° C.

2. The composition of claim 1 wherein the alcohol (a) is ethanol and the surfactant (f) is a nonionic surfactant.

3. The composition of claim 2 wherein the surfactant (f) is a nonionic surfactant selected from surfactants of the formula $R'O(CH_2CH_2O)_xH$ where R' is a hydrocarbon radical of from about 12 to 22 carbon atoms and x has a value of from about 2 to 100.

4. The composition of claim 3 wherein hydrocarbon emollient (d) is petrolatum, fatty ester emollient (e) is isopropyl palmitate, fatty alcohol (g) is selected from the group consisting of myristyl alcohol, cetyl alcohol and stearyl alcohol, and humectant (h) is glycerine.

5. The composition of claim 4 wherein the fatty alcohols present are cetyl alcohol and myristyl alcohol in a weight ratio of 2:1 to 5:1.

6. The composition of claim 4 wherein the neutralizing agent (c) is $(CH_3CH(OH)CH_2)_2NH$.

7. A high alcohol content gel composition with skin moisturizing and conditioning properties comprising
   (a) from about 60 to 65 weight percent of ethanol;
   (b) from about 0.45 to 0.65 weight percent of a thickening agent which is an addition polymer of acrylic acid crosslinked with an unsaturated polyfunctional agent;
   (c) a sufficient amount of a compatible neutralizing agent for thickening agent (b) to neutralize from about 15% to 50% of acrylic acid carboxyl units present in thickening agent (b), said neutralizing agent being selected from the group consisting of amines of the formula $HO(C_mH_{2m})_2NH$ where m has a value of from 2 to 3, aminomethyl propanol, aminomethyl propanediol, and $H(OCH_2CH_2)_xRN(CH_2CH_2O)_yH$ where R is a hydrocarbon radical having from 10 to 18 carbon atoms and the sum of x+y has an average value of from about 5 to 25;
   (d) from about 0.75 to 2 weight percent of at least one hydrocarbon emollient selected from the group consisting of petrolatum and mineral oil;
   (e) from about 0.5 to 1.5 weight percent of at least one fatty ester emollient;
   (f) from about 0.1 to 0.5 weight percent of at least one compatible surfactant to stabilize the composition;
   (g) from about 1 to 2.5 weight percent of at least one fatty alcohol having from 12 to 22 carbons atoms;
   (h) from about 2 to 4 weight percent of a humectant selected from the group consisting of water soluble polyhydric alcohols having from 2 to 3 hydroxyl groups;
   (i) up to about 0.5 weight percent of a compatible hydroxypropyl guar gum thickening agent; and
   (j) the balance comprising water, there being at least about 20 weight percent water present and the gel composition has a viscosity of from about 10,000 centipoise to 50,000 centipoise at 25° C.

8. The composition of claim 7 wherein the surfactant (f) is a nonionic surfactant, the amount of neutralizing agent (c) is such that from about 15% to 35% of the carboxyl units present in thickening agent (b) are neutralized and the amount of water present is at least 25 weight percent of the composition.

9. The composition of claim 8 wherein the nonionic surfactant is selected from surfactants of the formula $R'O(CH_2CH_2O)_xH$ where R' is a hydrocarbon radical of from about 12 to 22 carbon atoms and x has a value of from about 2 to 100.

10. The composition of claim 9 wherein hydrocarbon emollient (d) is petrolatum, fatty ester emollient (e) is isopropyl palmitate, fatty alcohol (g) is selected from the group consisting of myristyl alcohol, cetyl alcohol and stearyl alcohol, and humectant (h) is glycerine.

11. The composition of claim 10 wherein the fatty alcohols present are cetyl alcohol and myristyl alcohol in a weight ratio of 2:1 to 5:1.

12. The composition of claim 10 wherein the neutralizing agent (c) is $(CH_3CH(OH)CH_2)_2NH$.

* * * * *